United States Patent
Wang et al.

(10) Patent No.: US 9,970,065 B2
(45) Date of Patent: May 15, 2018

(54) **REAL-TIME PCR ASSAY FOR DETECTION OF *BABESIA MICROTI* AND CLINICAL UTILIZATION IN DIAGNOSIS AND TREATMENT OF BABESIOSIS**

(71) Applicant: WESTCHESTER MEDICAL CENTER ADVANCED PHYSICIAN SERVICES, PC, Hawthorne, NY (US)

(72) Inventors: Guiqing Wang, Ossining, NY (US); John T. Fallon, Rowayton, CT (US)

(73) Assignee: Westchester Medical Center Advanced Physician Services, PC, Hawthorne, NY (US)

( * ) Notice: Subject to any disclaimer, the term of this patent is extended or adjusted under 35 U.S.C. 154(b) by 447 days.

(21) Appl. No.: 14/613,431

(22) Filed: Feb. 4, 2015

(65) Prior Publication Data
US 2015/0218657 A1 Aug. 6, 2015

Related U.S. Application Data

(60) Provisional application No. 61/935,386, filed on Feb. 4, 2014.

(51) Int. Cl.
*C12Q 1/68* (2018.01)

(52) U.S. Cl.
CPC ......... *C12Q 1/6893* (2013.01); *C12Q 1/6883* (2013.01); *C12Q 2600/16* (2013.01)

(58) Field of Classification Search
None
See application file for complete search history.

(56) References Cited

PUBLICATIONS

Wang and Seed. (2006) High-throughput primer and probe design. In M. Tevfik Dorak (Ed.), Real-time PCR (pp. 93-105). New York, New York: Taylor & Francis Group.*
La Paz et al. Journal of Agricultural and Food Chemistry 2007; 55: 4312-4318.*
Bloch, Em et al., Development of a real-time polymerase chain reaction assay for sensitive detection and quantitation of Babesia microti infection. Transfusion 53: 2299-2306, 2013.
Chan K et al., entitled Sensitive multiplex PCR assay to differentiate Lyme spirochetes and emerging pathogens Anaplasma phagocytophilum and Babesia microti, BMC Microbiology 2013, 13:295, 15 pages.
Hojgaard, A. et al., Detection of Borrelia burgdorferi, Anaplasma phagocytophilum and Babesia microti, with two different multiplex PCR assays. Ticks and Tick-borne Diseases 5(3)349-51. Epub Jan. 18, 2014.
Rollend L et al., entitled "Quantitative PCR for Detection of Babesia microti in Ixodes scapularis Ticks and in Human Blood," Vector-Borne and Zoonotic Diseases, vol. 13, No. 11, 2013, pp. 784-790.
Teal A E, et al., entitled "A New Real-Time PCR Assay for Improved Detection of the Parasite Babesia microti," Journal of Clinical Microbiology, Mar. 2012;50(3):903-908. Epub Dec. 14, 2011.

* cited by examiner

*Primary Examiner* — Angela M. Bertagna
(74) *Attorney, Agent, or Firm* — Amster, Rothstein & Ebenstein LLP

(57) ABSTRACT

Methods and kits are provided for detecting *Babesia microti* using real-time polymerase chain reaction.

5 Claims, 2 Drawing Sheets

```
                                    165----------------------185   189----------------------------214         226---------------243
AY048113_MO1 isolate     GGCCT----TTT------GGCGGCGTTTATTAGTTCTA-AAACCATCCCTTTT-----GGTT--TTCGGTGATTCATAATAAACT TGCGAATCGCAATTTTTT-GC----GATGG
U16370_B_divergens       GGCCT----TTT------GGCGGCGTTTATTAGTTCTA-AAACCATCCCTTTT-----GGTT--TTCGGTGATTCATAATAAACT TGCGAATCGCAATTTTTT-GC----GATGG
GU647159_EU1 isolate     GGCCT----TTT------GGCGGCGTTTATTAGTTCTA-TAACCACCC-TTTT-----GGTT--TTCGGTGATTCATAATAAACT CGCGAATCGCAATTTATT-GC----GATGG
U16369_B_odocoilei       GGCCT----TTTT-----GGCGGCGTTTATTAGTTCTA--AACCATCCGTTTT-----GGTT--TTCGGTGATTCATAATAAACT CGCGAATCGCAATTTATT-GC----GATGG
AF175300_B_gibsoni       GGCCT----TTTT-----GGCGGCGTTTATTAGTTCTA--AACCTCCC---TT-----GGTT--TTCGGTGATTCATAATAAACT CGCGAATCGC---TTTTA-GC----GATGG
L19079_B_canis           GGCCT----TTT------GGCCGCGTTTATTAGTTGTA--AACCTCCG--CTT-----GGTT--TTCGGTGATTCATAATAAACT TGCGAATCGC---TTTTA-GC----GATGG
Z15104_B_caballi         TGCCT----TTT------GGCGGCGTTTATTAGTTTTT--AACC-------CT-----TATT--TTCGGTGATTCATAATAAACT TGCGAATCGC--TTTTGA-GC----GATGG
X59604_B_bigemina        GGCCT----TTT------GGCGGCGTTTATTAGTTCGT-TAACCAC-----TT-------TT--TCTGGTGATTCATAATAAACT TGCGAATCGC----TTTT-GC----GATGT
L19077_B_bovis           GGGTT----TTC--------CCGCGTTTACTGGTCTT------------------------------GTGATTTACAGTAA-CC TGCGACTCGC---TTTTT-GC----GATAT
Z15105_B_equi            GCTGT----TTAC-----AGTTGCGTTTATTAGACCTA-AAACCTCCCCGCTTCTGCGGTGT--TTCGGTGATTCATAATAAATT AGCGAATCGCATGGCTTT-GCCGGCGATGT
M93660_Bm                GGCGCGT-TTTC-----GCGTGGCGTTTATTAGACTT--TAACCAACCC--TTC---GGGT--AATCGGTGATTCATAATAAATT AGCGAATCGCATGGCTTT-GCCGGCGATGT
AB190459_Bm_30222        GGCGCGT-TTTC-----GCGTGGCGTTTATTAGACTT--TAACCAACCC--TTC---GGGT--AATCGGTGATTCATAATAAATT AGCGAATCGCATGGCTTT-GCCGGCGATGT
AY693840_Bm_Gray         GGCGCGT-TTTC-----GCGTGGCGTTTATTAGACTT--TAACCAACCC--TTC---GGGT--AATCGGTGATTCATAATAAATT AGCGAATCGCATGGCTTT-GCCGGCGATGT
EF413181_Bm_Jena         GGCGCGT-TTTC-----GCGTGGCGTTTATTAGACTT--TAACCAACCC--TTC---GGGT--AATCGGTGATTCATAATAAATT AGCGAATCGCATGGCTTT-GCCGGCGATGT
AB197940_Bm_Japan        GGCATATACTTCTGTATATGTGGCGTTTATTAGACTTCTTAACCAACCCCTTTT---GGGTTTACTCGGTGATTCATAATAAATT AGCGAATCGCATGGTYCT-ACCGGCGATAT
AY027815_WA1 isolate     GGCCTTGGCTTCTGTCTTGGCTGCGTTTATTAGACTCG-AAACCTTCCCGCTTG---CGGT--ACTCGGTGATTCATAATAAATT TGCGAATCGCATGGCTTTTGCCGGCGATGG
                                    **           ******* * *                             ****** * * ***       **** ****         *    ***
                                    SEQ ID NO: 1                 SEQ ID NO: 3                                 (SEQ ID NO: 2 is complementary
                                                                                                                reverse sequence)
```

REAL-TIME PCR ASSAY FOR DETECTION OF *BABESIA MICROTI* AND CLINICAL UTILIZATION IN DIAGNOSIS AND TREATMENT OF BABESIOSIS

CROSS-REFERENCE TO RELATED APPLICATION

This application claims the benefit of U.S. Provisional Patent Application No. 61/935,386, filed Feb. 4, 2014, the content of which is herein incorporated by reference in its entirety.

BACKGROUND OF THE INVENTION

Throughout this application various publications are referred to in parentheses. Full citations for these references may be found at the end of the specification. The disclosures of these publications are hereby incorporated by reference in their entirety into the subject application to more fully describe the art to which the subject invention pertains.

Babesiosis is an emerging tick-borne disease caused by protozoan parasites of the genus *Babesia* that infects red blood cells (1, 2). *Babesia* infection can range from asymptomatic in healthy, immunocompetent persons to severe, life threatening syndromes such as hemolytic anemia, thrombocytopenia, organ failure, and even death, in individuals at risk, i.e., the elderly, asplenic persons, and those with coincident Lyme disease (3). Although babesiosis usually resolves in 2 to 3 weeks in immunocompetent individuals, there are reports of individuals carrying a low-grade asymptomatic infection for more than 2 years.

*Babesia* parasites in nature usually are transmitted to humans and animals by *Ixodid* ticks. The *Ixodid* ticks also transmit *Borrelia burgdorferi* and *Anaplasma phagocytophilum*, the etiologic agents for Lyme disease and Anaplasmosis, respectively. The *Babesia* parasites also are transmissible via blood transfusion or congenitally (4-7). In recent years, reports of tick-borne and transfusion-associated babesiosis cases have increased in number and geographic distribution in the United States. Because babesiosis may be asymptomatic, blood donors may not realize that they are infected, which poses a risk to the blood supply in areas of high endemicity. Between 1979 and 2009 over 159 transfusion-related *B. microti* cases, including nine deaths, have been documented in the U.S. (6, 8). Transmission of the *Babesia* parasites by transfusion is of particular concern, since recipients are likely to be in suboptimal health and less able to mount an efficient immune response: this could lead to rapid development of high parasitemia and difficulty clearing the infection.

In response to its increasing public health threat, the Centers for Disease Control and Prevention (CDC) made babesiosis a nationally notifiable disease as of January 2011 and received 1,124 cases reported from 15 states in 2011. To date all babesiosis cases reported to CDC with species-level information are caused by infection of *Babesia microti*, which occur mainly in the Northeast from coastal regions to areas such as inland counties of the lower Hudson River Valley of New York State, and some upper Midwest states such as Minnesota and Wisconsin (9-11). Human babesiosis is less common in Europe, where it is most often caused by infection with *Babesia divergens* (12).

The national surveillance case definition for babesiosis developed jointly by CDC and the Council of State and Territorial Epidemiologists recommends to confirm a diagnosis by one of the following laboratory methods: i) identification of intraerythrocytic *Babesia* organisms by light microscopy in a Giemsa, Wright, or Wright-Giemsa-stained blood smear; or ii) detection of *Babesia microti* DNA in a whole blood specimen by polymerase chain reaction (PCR); or detection of *Babesia* spp. genomic sequences in a whole blood specimen by nucleic acid amplification; or iii) isolation of *Babesia* organisms from a whole blood specimen by animal inoculation. Among these, animal inoculation is not a practical option. Therefore, microscopic examination of blood smears is currently the gold standard assay for confirmation of *Babesia* infection. However, this assay requires specially trained personnel for analysis, and has a detection of limit of 10-100 parasites/microtiter, which limits its use in patients with low parasitemia (13). Also, the infecting *Babesia* species can only be identified to the genus level based on morphological criteria. Furthermore, *Babesia* parasites can be difficult to distinguish from the early trophozoite (ring form) of *Plasmodium* parasites, particularly *P. falciparum*, in which ring forms are often the only stage that is observed. Thus, improved laboratory assays are needed both for clinical diagnosis and patient management, and for blood donor screening to prevent transfusion-transmitted babesiosis. DNA amplification using PCR is recognized as the most sensitive and specific methods for confirmation of *B. microti* infection and blood donor screening (14-16). However, there are no U.S. Food and Drug Administration-approved tests for *Babesia*.

Recently, the use of real-time PCR has been described for detection of *B. microti* in ticks and clinical specimens from patients suspected of having tick-borne and transfusion-associated babesiosis (17-21). In these reports, the analytical sensitivity of real-time PCR assays was assessed by spiking cloned plasmid DNA to negative patient samples, which may result in inaccurate results due to the potential of preferred amplification of small plasmid DNA fragments rather than target sequence from the complete genome of a parasite in the PCR reaction (22, 23). Moreover, there are very limited data available on their clinical utilization in diagnosis and monitoring of treatment in patients.

The present invention addresses these needs by providing a validated, real-time PCR assay for rapid and accurate detection of *B. microti*.

SUMMARY OF THE INVENTION

The present invention provides methods of detecting *Babesia microti* (*B. microti*) using real-time polymerase chain reaction comprising amplifying nucleic acid from *B. microti* using forward primer CGCGTGGCGTTTATTAGACTT (SEQ ID NO: 1), reverse primer CAAAGCCATGCGATTCGC (SEQ ID NO:2), and probe CCAACCCTTCGGGTAATCGGTGATTC (SEQ ID NO:3) to thereby detect *B. microti*.

The invention also provides kits for detecting *Babesia microti* (*B. microti*) using real-time polymerase chain reaction comprising
- forward primer CGCGTGGCGTTTATTAGACTT (SEQ ID NO: 1),
- reverse primer CAAAGCCATGCGATTCGC (SEQ ID NO:2),
- probe CCAACCCTTCGGGTAATCGGTGATTC (SEQ ID NO:3)

and instructions for use.

BRIEF DESCRIPTION OF THE DRAWINGS

FIG. 1. DNA sequence alignment and primer/probe sequence. Sequence identifiers: forward primer (underlined region)—SEQ ID NO: 1, probe (underlined region)—SEQ ID NO:3, MO1 isolate—SEQ ID NO:4, *B. divergens*—SEQ ID NO:5, EU1 isolate—SEQ ID NO:6, *B. odocoilei*—SEQ ID NO:7, *B. gibsoni*—SEQ ID NO:8, *B. canis*—SEQ ID NO:9, *B. caballi*—SEQ ID NO:10, *B. bigemina*—SEQ ID NO:11, *B. bovis*—SEQ ID NO:12, *B. equi*—SEQ ID NO:13, Bm—SEQ ID NO:14, Bm 30222—SEQ ID NO:15, Bm Gray—SEQ ID NO:16, Bm Jena—SEQ ID NO:17, Bm Japan—SEQ ID NO:18, WA1 isolate—SEQ ID NO:19. Reverse primer SEQ ID NO:2 is the complementary reverse sequence of the underlined sequence in the right side of the figure.

DETAILED DESCRIPTION OF THE INVENTION

Figure 2:
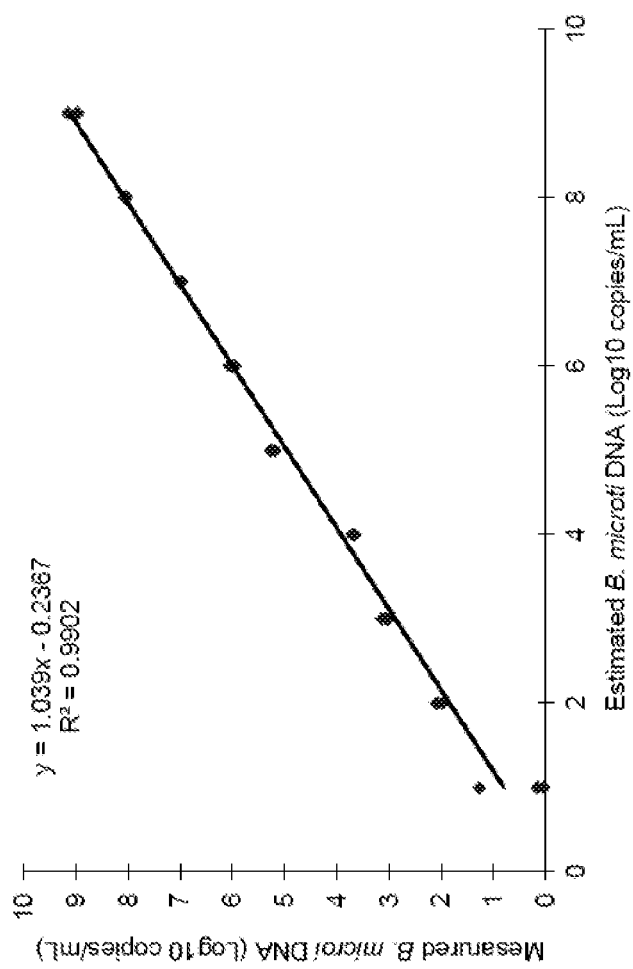
FIG. 2. Linearity of the *B. microti* DNA PCR.

The present invention provides a method of detecting *Babesia microti* (*B. microti*) using real-time polymerase chain reaction comprising amplifying nucleic acid from *B. microti* using forward primer CGCGTGGCGTTTATTA-GACTT (SEQ ID NO: 1), reverse primer CAAAGCCAT-GCGATTCGC (SEQ ID NO:2), and probe CCAACCCT-TCGGGTAATCGGTGATTC (SEQ ID NO:3) to thereby detect *B. microti*.

The invention also provides a kit for detecting *Babesia microti* (*B. microti*) using real-time polymerase chain reaction comprising
  forward primer (5'>3'): CGCGTGGCGTTTATTA-GACTT (SEQ ID NO:1).
  reverse primer (5'>3'): CAAAGCCATGCGATTCGC (SEQ ID NO:2),
  probe (5'>3'): CCAACCCTTCGGGTAATCGGTGATTC (SEQ ID NO:3)
  and instructions for use.

The primers and probes described herein are designed to target the 18S rRNA gene (GenBank accession number AB190459) of *B. microti*.

The probe can be labelled with a fluorescent reporter that permits detection only after hybridization of the probe with its complementary sequence. In preferred embodiments, the probe is labeled with 6-carboxyfluorescein (FAM) at the 5' terminal and tetramethylrhodamine (TAMRA) at the 3' terminal. Alternatively, fluorescent dyes such as TET™, VIC, JOE™ or NED™ can be used to replace FAM.

Real-time PCR is a routine procedure known to those of ordinary skill in the art (e.g., U.S. Patent Application Publication Nos. 2003/0219788, 2004/0191822, 2010/0105033, the contents of which are incorporated herein by reference).

Preferably, *B. microti* is detected in a sample from blood, such as for example blood from a human patient or human blood from a blood bank. The methods and kits disclosed herein can detect as few as 1-3 *B. microti* per microtiter of blood. The kits and methods disclosed herein can also be used to detect *B. microti* in the blood of non-human animals, such as for example in veterinary practice and from tick vectors.

Preferably, the methods and kits disclosed herein do not detect any of *B. divergens, B. bovis, B. cabalii, B. gasoni, B. odocoilei*, and *Theileria [Babesia] equi*. Preferably, the methods and kits disclosed herein do not detect any of *B. burgdorferi, Anaplasma phagocytophilum, Bartonella henselae, Plasmodium falciparum, P. vixax, P. ovale, P. malarie, Leishmania* sp., *Trypanosoma brucei*, Herpes simplex virus (HSV)-1 and 2, Cytomegalovirus (CMV), Epstein-Barr virus (EBV), enterovirus, Human immunodeficiency virus-1 (HIV-1), Hepatitis C virus (HCV), Hepatitis B virus (HBV), *Bartonella henselae, Staphylococcus aureus, S. epidermidis, S. lugdunensis, Enterococcus* sp., *Escherichia coli, Pseudomonas aeruginosa, Klebsiella pneumoniae, Candida albicans, Cryptococcus neoformans*, and *Aspergillus* sp.

The kits disclosed herein can also contain a set of external standards for quantifying the amount of *B. microti* in a sample.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Overview

Babesiosis is an emerging zoonosis with important public health implications, as the incidence of the disease has risen dramatically over the past decade. Because the current gold standard for detection of *Babesia* is microscopic examination of blood smears, accurate identification requires trained personnel. Species in the genus cannot be distinguished microscopically, and *Babesia* can also be confused with the early trophozoite stage of *Plasmodium* parasites. In this study, a real-time PCR assay was developed that targets the 18S rRNA gene of *Babesia microti*, the dominant babesiosis pathogen in the United States. The real-time PCR is performed on DNA extracted from whole-blood specimens and detects *Babesia microti* with a limit of detection of 0.36-2.7 parasites per microtiter of blood, or 7.2-54 parasites per PCR reaction. The real-time PCR assay was shown to be 100% specific when tested against a panel of 61 organisms consisting of other *Babesia* species, *Plasmodium* species, tick-borne and pathogenic bacteria, and other blood-borne parasites. The results using clinical specimens show that the assay can detect infections of lower parasitemia than can be detected by microscopic examination. This method is therefore a rapid, sensitive, and accurate method for detection of *B. microti* in clinical patient specimens and potentially for blood donor screening.

The DNA sequences and real-time PCR protocol described in this application were evaluated for analytical performance per guidelines of the New York State Department of Health (NYSDOH) Clinical Laboratory Evaluation Program (CLEP). This test was highly accurate for detection of *B. microti* in patient blood samples with a diagnostic sensitivity of 100% and specificity of 99.3%. It was approved by the NYSDOH on Sep. 28, 2012 for in vitro diagnostic testing of patient specimens in clinical laboratory (Project ID: 27607).

Materials and Methods

Selection of PCR Primers and Probe.

The DNA target for this assay is a variable region of the 18S rRNA gene (GenBank accession number AB190459) that contains sequence that is species-specific for *B. microti*. PCR primers and probe were designed using both Primer3 (worldwideweb.ncbi.nlm.nih.gov/tools/primer-blast) and Primer Express (Applied Biosystems, Foster City Calif.) and chosen on the basis of GC content and lack of hairpin structures.

To ascertain that the PCR primer/probe combination was specific for *B. microti*, the DNA target sequence on the 18S rRNA gene was compared with orthologous sequences from other *Babesia* species known to infect humans and animals using ClustalW and MEGA. These include *B. divergens*

(U16370), *B. duncani* WA1 (AY027815), *B. bovis* (L19077), *B. equi* (Z15105), *B. gibsoni* (AF175300), *B. bigemina* (X59604), *B. odocoilei* (U16369) and *Babesia* sp. MO1 (AY048113). The aligned sequences of *Babesia* spp. and related species and the sequences of *B. microti*-specific primers and probe are given in FIG. 1. The forward primer starts at position 165, the reverse primer starts at position 243, and the probe starts at position 189. This primer/probe combination is predicted to amplify the DNA of *B. microti* strains with an amplion size of 79-bp.

Clinical Sample and DNA Extraction.

Aliquots of EDTA-anticoagulated whole blood specimens submitted to the Westchester Medical Center Clinical Laboratories for identification or confirmation of blood parasites, including infection of *Babesia*, during January 2009 through October 2013. Blood samples are evaluated by Giemsa-stained thick and thin blood smears, as well as nucleic acid amplification. At least 300 oil-immersion fields were examined before calling a specimen negative.

DNA was extracted from 200 µl of EDTA-preserved whole blood using the QIAamp DNA Blood Mini kit for blood and body fluids protocol (Qiagen, Germantown Md.) according to the manufacturer's instructions and eluted in 100 µl of elution buffer. For each PCR run. DNA was also extracted from a negative control consisting of previously tested blood that did not contain *B. microti* and a positive control consisting of diluted blood that was previously tested positive for *B. microti*.

*B. microti* Multiplex Real-Time PCR Assay.

The *B. microti* multiplex real-time PCR assay was performed on the 7500 Fast Dx Real-Time PCR instrument (Applied Biosystems, Foster City Calif.). The PCR reaction consisted of 2× Taqman® Fast Universal PCR Master Mix (no AmpErase, Applied Biosystems, Foster City Calif.), 0.9 µM forward and reverse primers and 0.2 µM probe that are specific for *B. microti*, and 0.01 µm forward and reverse primers and 0.1 µm probe that are specific for human gapdh gene. Five microliters of extracted DNA template was added to each reaction in a total volume of 20 µL. Cycling conditions were as follows: 50° C. for 2 min, 95° C. for 10 min, followed by 40 cycles of denaturation at 95° C. for 15 s, and annealing at 60° C. for 20 s. Primers and probes used were for *B. microti* 18S rDNA, forward primer CGCGTG-GCGTTTATTAGACTT (SEQ ID NO:1), reverse primer CAAAGCCATGCGATTCGC (SEQ ID NO:2), and probe FAM-CCAACCCTTCGGGTAATCGGTGATTC-TAMRA (SEQ ID NO:3), and for human gapdh, forward primer CCTGCCAAATATGATGACATCAAG (SEQ ID NO:20), reverse primer GTGGTCGTTGAGGGCAATG (SEQ ID NO:21), and probe VIC-CTCCTCTGACTTCAACAGC-GACACCCA-TAMRA (SEQ ID NO:22) (sequences are listed 5'>3').

Analytical Sensitivity of *B. microti* PCR Assay.

The analytical sensitivity of the PCR assay was assessed by two different approaches: First, a series of seven 10-fold dilutions was prepared by directly spiking a positive patient sample with known percentage of *B. microti* parasitemia into pooled-negative patient blood specimens. Second, a *B. microti*-positive control was constructed by cloning the 79-bp PCR amplicon into a pUC108 plasmid (Invitrogen). A series of eight 2- to 10-fold dilutions was prepared from uninfected human blood spiked with known amounts of this plasmid DNA (5, 50, 250, 500, 2500, 5000, 50000 and 500000 copies/mL). For both dilution series, DNA was extracted from spiked blood samples and analyzed in duplicate or triplicate on three different days to determine the lower limit of *B. microti* DNA detection. The Probit analysis was employed to determine the limit of detection of the *B. microti* DNA PCR assay by using the SPSS software (IBM, ver. 14). Additional series with nine dilutions containing 10 to $10^9$ copies of cloned *B. microti* plasmid DNA in human blood were also prepared and analyzed in triplicate to determine the linearity and efficiency of amplification of this PCR assay.

Analytical Specificity of *B. microti* PCR Assay.

The analytical specificity of the *B. microti* DNA PCR assay was evaluated by testing a collection of 61 specimens known to be positive for various microorganisms. These included parasites from 6 closely-related *Babesia* species (*B. divergens, B. bovis, B. cabalii, B. gasoni, B. odocoilei,* and *Theileria* [*Babesia*] *equi*), tick-borne pathogens (*B. burgdorferi, Anaplasma phagocytophilum, Bartonella henselae*), other blood parasites (*Plasmodium falciparum, P. vixax, P. ovale, P. malarie, Leishmania* sp., *Trypanosoma brucei*), and a variety of viruses that may be detected in patient blood specimens (i.e., HSV, CMV, EBV, enterovirus, HIV-1, HCV, HBV). ATCC quality control or clinical bacterial and fungal organisms (*Bartonella henselae, Staphylococcus aureus, S. epidermidis, S. lugdunensis, Enterococcus* sp., *Escherichia coli, Pseudomonas aeruginosa, Klebsiella pneumoniae, Candida albicans, Cryptococcus neoformans,* and *Aspergillus* sp.) were also examined for cross-reactivity by the *B. microti* DNA PCR test.

In addition, the interference testing was performed by spiking a known low level of *B. microti*-infected blood specimen into negative blood specimens with various levels of interfering substances (AcroMetrix™ inhibition panel). The measured *B. microti* DNA in each spiked specimen was compared to that recovered from the EDTA blood control. PCR inhibition is considered to be significant if there is >2.0 decrease in the Ct value of specimen with interfering substance compared to that of the EDTA blood control.

Clinical Sensitivity and Specificity of *B. microti* PCR Assay.

To assess the diagnostic value of this multiplex real-time PCR assay, blood Giemsa-smear results and clinical data from each patient were reviewed. The clinical sensitivity of the *B. microti* DNA real-time PCR assay was assessed by comparing results obtained from PCR and blood Giemsa-stained smears, the current gold standard for detection of *Babesia* infection. Selective patient specimens were also analyzed by the NYSDOH Wadsworth Center Parasitology Laboratory using a real-time PCR assay (17). For patient specimens with discrepant results between Giemsa smear and PCR, clinical and other laboratory test results were reviewed and used to determine if the patient had an infection by *B. microti*.

Data Analysis.

Statistical analysis was performed using the Mann-Whitney test, column statistics and linear regression programs of the Prism 5 software (GraphPad Software, La Jolla, Calif.).

Study approval. This study was part of ta clinical laboratories quality improvement program. Review of patient medical records was approved by the New York Medical College Office of Research Administration.

Results

Limit of Detection of *B. microti* PCR Assay.

The analytical sensitivity of *B. microti* PCR assay was evaluated in two different experiment using spiked blood dilutions directly prepared from positive patient blood or cloned plasmid DNA.

In the first experiment, parasitemia levels of $5.0 \times 10^{-3}$ to $5.0 \times 10^{-9}$% infected RBCs were prepared by spiking a fresh patient blood sample with 5% *B. microti* parasitemia, in which the total RBC count was 4.14×10⁶ RBC/μl, into a *B. microti*-negative human blood specimen. The limit of detection of *B. microti* DNA by the PCR was determined by the PROBIT analysis to be 0.000065% (6.5×10⁻⁵%) parasite infected RBCs, with a positive rate greater than 95%. This corresponded to 2.7 parasites/μl of blood, or 54 parasites per PCR reaction, using the assumption of one parasite per infected RBC (Table 1).

In the second experiment, eight dilutions of blood samples were prepared from uninfected human blood spiked with known target concentrations of plasmid DNA. The limit of detection of the *B. microti* DNA PCR was determined by the PROBIT analysis as 715 copies of *B. microti* DNA per mL of blood for a positive rate greater than 95%, corresponding to 0.36 parasites/μl of blood, or 7.2 parasites per PCR reaction, assuming that there are two copies of rDNA units per parasite cell.

The linearity of the assay was determined by plotting cycle threshold versus copy number for the dilution series of the control plasmid used in the previous experiment (FIG. 2). This PCR assay was capable to detect over 8 log of *B. microti* DNA. The slope was found to be −3.50, with an $R^2$ of 0.990, which is very close to the theoretical optimum of 1.0. The calculated PCR efficiency was 95.0%. Therefore, this assay could be expanded as a quantitative assay to estimate gene copy number and, by extension, percent parasitemia in clinical samples.

Analytical Specificity.

No cross-reactivity of the testing organisms was observed by the *B. microti* DNA PCR assay. Elevated levels of hemoglobin (0.5, 1.0 and 2.0 g/dL), triglycerides (0.75 g/dL) and bilirubin (16 mg/dL) in specimens showed not to interfere with the detection of *B. microti* DNA by the *B. microti* DNA PCR assay. However, heparin affects slightly the PCR amplification efficiency.

To confirm specificity of the assay, PCR amplicons from 5 positive clinical specimens were obtained and sequenced using the ABI 3500xl Genetic Analyzer. Sequence analysis of the PCR amplicons confirmed that all 5 amplicons contained *B. microti*-specific sequence as expected.

Reproducibility.

The intra-assay reproducibility of the *B. microti* DNA PCR was evaluated by running three levels of spiked blood specimens from DNA extraction in one day. Triplicate PCR wells were set up for each extracted DNA. Therefore, for each positive sample 9 replicates were obtained from this intra-assay reproducibility study. The parasitemia of these positive samples varied from 5.0×E−5% (near the LOD) to 5.0×E−3(%). As shown in Table 2, a high intra-assay reproducibility was demonstrated with a standard derivation (SD) on the Ct value of less than 0.56 and a coefficiency of variance (CV) of <1.5%.

The inter-assay reproducibility of the *B. microti* DNA PCR was demonstrated by testing three levels of spiked blood specimens in three different days. Duplicate samples were subjected for DNA extraction and PCR analysis on each day. A total of 6 replicates were obtained from this inter-assay reproducibility testing for each positive sample. For the two specimens with parasitemia levels above than the LOD of the assay, the inter-assay CV % of the *B. microti* DNA PCR were 1.1% and 2.3%, respectively. A third specimen had a parasitemia below the LOD of the assay and 67% (4 of 6 replicates) reproducibility. Also, the inter-assay reproducibility of *B. microti* DNA PCR was analyzed by repeated testing of the low positive quality control sample for 21 days. The mean Ct, SD and CV % for this sample was 32.1, 1.3 and 3.9%, respectively.

Comparison of PCR to Giemsa Smear Results.

The clinical sensitivity and specificity of *B. microti* PCR assay were assessed by comparing results obtained by PCR and microscopic examination of Giemsa-stained blood smears. A total of 145 patient blood specimens were analyzed. Compared to the routine microscopic examination on Giemsa smears, the accuracy of the *B. microti* DNA PCR was 97.9% with a sensitivity of 100% and a specificity of 97.7%. Discrepant results were observed for three (n=3) patient specimens. These three specimens were negative by Giemsa stain but were positive for *B. microti* DNA at the WMC Laboratory. Of these, two specimens were positive by PCR at the Wadsworth Laboratory. The adjusted accuracy was 99.3% with a sensitivity of 100% and a specificity of 99.2%. One specimen yielded a low positive (Ct=37.2) by PCR at the WMC Laboratory but was negative at the Wadsworth Laboratory. Review of clinical and laboratory data confirmed that this specimen was collected from a patient recently diagnosed as babesiosis and underwent anti-parasitic treatment.

Fifty-eight patient blood specimens were also analyzed by a real-time PCR assay at a reference laboratory (Table 4). Compared to the reference laboratory *B. microti* real-time PCR assay, this *B. microti* DNA PCR showed a diagnostic sensitivity of 100% and a specificity of 97.6%.

Performance of the Assay in Routine Clinical Testing.

The assay has been used to evaluate 260 peripheral blood samples from 222 patients submitted to the laboratory for identification or confirmation of *Babesia* infection. Forty-six samples from 19 patients were positive by PCR. Of these, 16 (84.2%) patients were also positive by microscopic examination of Giemsa-stained blood smears. The parasitemia among the smear-positive patient varies from 0.01% to 15%. The cycle threshold ($C_T$) values for the smear-positive samples were low (mean, 21.6; median, 20.7; range, 18.2 to 29.3), a finding consistent with the high parasitemia. Three PCR-positive patients were negative by Giemsa-stained smears. The mean $C_T$ value of smear-negative patient specimen was 29.1, which was significantly higher than that of smear-positive specimens, suggesting lower parasitemia in these blood specimens. Also, it is noteworthy that 23 follow-up specimens from the 16 smear-positive patients were positive by PCR but were negative by Giemsa-stained smears, suggesting that the PCR assay was also able to improve parasite detection in a patient who was slowly clearing an infection. A summary of the performance of *B. microti* DNA PCR in comparison with microscopy for 185 blood samples from 152 patients as routine testing in a prospective study is shown in Table 5.

Diagnosis and Management of Patients with Babesiosis.

Using real-time quantitative PCR (qPCR) with the primers and probe described in this application, the number of DNA copies/mL of blood of a *Babesia microti* gene was determined in infected patients. Thirty-six patients (whose median age was 62.5 years and 75.0% were male) with at least one qPCR positive blood sample were included in this analysis, including 16 with serial blood samples. Based on testing of serial blood samples, it could be demonstrated that the smear became negative while the qPCR remained positive. A moderate to strong correlation was found between the quantitative DNA copy number and the number of infected erythrocytes/mL of blood (Pearson's r=0.68, p<0.001). The DNA copy number fell by a mean of 4.1% to 12.9% per day on active treatment and by 3.5% to 7.1% per day off therapy. qPCR methodology can permit systematic evaluations of the relative efficacy of various anti-parasitic drug regimens and other therapeutic modalities. Also, this test was employed successfully for diagnosis and monitoring of anti-*babesia* treatment in a patient with congenital babesiosis.

Discussion

These studies provide a highly sensitive and specific *B. microti* PCR assay that can successfully amplify low copies of *B. microti* DNA in human blood samples. The assay is unique in several aspects: First, unlike few published real-time PCR tests that use only cloned plasmid DNA to evaluate the assay's limit of detection, the analytical sensitivity of this PCR assay was demonstrated by analyzing blood specimens directly spiked with a positive patient sample with known parasitemia. Since the estimation of percent parasitermia in patient sample is less variable than that to estimate the copy number of target gene in cloned plasmid per measured DNA concentration, the analytical sensitivity determined by this assay is more reliable and clinical relevant. It also eliminates the potential biased amplification and PCR efficiency between plasmid DNA and patient sample with much larger genomic DNA content. Second, a multiplex PCR approach was employed, in which a human housekeeping gene was selected and co-analyzed for each sample. In the multiplex PCR, the primer and probe concentrations for the housekeeping gene in the PCR reaction were optimized not to interfere amplification of *B. microti*-specific target but provided reliable data in monitoring the input specimen adequacy and the presence of PCR inhibitors. Therefore, an external 'internal control' is not required for patient samples to be analyzed. Third, a higher specificity of this PCR assay is warranted by analysis of both theoretically aligned sequences and actual experimental data. A recently developed real-time PCR (17) for detection of *B. microti* infection in humans targeted also the 18S rRNA gene, but its primers and probe anneal to regions with less sequence mismatches to the other human *Babesia* species compared to the primers and probe used in the present assay. Last, the present PCR takes only approximately 40 minutes with the use of fast universal master mix reagents, providing more timely results to clinicians and blood centers for donor screening.

The *B. microti* PCR assay detects lower levels of *B. microti* DNA than Giemsa blood smear method and therefore provides a more sensitive determination of *B. microti* infection in human blood. It can detect as few as 1-3 parasites per microliter of whole blood. Since the average detection limit by microscopy is about 100 parasites/µl, the present *B. microti* DNA PCR is about 30-100× more sensitive than microscopic examination of blood smears. It, therefore, provides a more sensitive testing method for detection of *B. microti* infection. In addition, the assay has an excellent linearity of response over 8 orders of magnitude. With the inclusion of a set of external standards to generate a calibration curve, this assay can be converted to a quantitative test that permits calculation of the percent parasitemia, which is potentially important for treatment since the disease can reach high levels of parasitemia quickly.

The results using clinical specimens show that the assay can detect infections of lower parasitemia than can be detected by microscopic examination. This procedure takes less than 2 hours method is a rapid, sensitive, and accurate method for detection of *B. microti* in patient specimens. The assay is also helpful in cases where parasites may be difficult to detect by microscopic methods. This can occur when there is a delay between collection of the sample and receipt by the laboratory, and the whole blood sample is received hemolyzed. Parasites in samples from patients that have been drug-treated can also be difficult to detect; this may be the case when treated patients still have a relatively high $C_T$ but no morphologically detectable parasites.

The *B. microti* PCR assay developed in this study does not amplify DNA from *B. burgdorferi*, and *A. phagocytophilum*, two pathogens that infect humans, and other closely related *Babesia* species, demonstrating excellent analytical specificity of the assay. On the basis of sequence alignment, it is unlikely that this PCR assay will amplify DNA from other *Babesia* species that infect humans in geographic regions beyond the northeast and northern midwest, including *B. duncani, B. divergens, B. venatorum*, and *Babesia* sp. MO-1. Some *Babesia* species or variants could not be tested in the present study due to the difficulty in obtaining DNA samples. Such high specificity of this PCR assay may limit its clinical utilization in areas with patients infected with non-*B. microti* species or variants. Although a few cases of *B. duncani* have been described in the northern Pacific coast and three cases of *B. divergens*-like organisms have been described in the U.S. (2, 21), the vast majority of human cases of babesiosis in the U.S. are caused by *B. microti*. Neither *B. duncani* nor *B. divergens* has been described in babesiosis-endemic areas of the Northeast or northern Midwest where *B. microti* is prevalent, nor have they been found in *I. scapularis* ticks.

In summary, a highly sensitive and accurate *B. microti* PCR assay has been developed that is superior to blood smear and can be used to detect *B. microti* in blood samples for the diagnosis and management of patients with babesiosis. This method may also be effective for screening donated blood, an important consideration in the face of the reports of transmission-associated infections described above.

TABLE 1

Limit of detection (LOD) of *B. microti* DNA PCR assay, determined using blood specimens spiked with a positive patient blood sample with a known level of parasitemia.

| Dilution | Parasitemia (%) | No. of infected RBC/µL[a] | No. of samples tested | No. of samples positive | Positivity (%) | Probability[b] |
|---|---|---|---|---|---|---|
| D | 5.00E−03 | 210 | 9 | 9 | 100.0 | 1.000 |
| E | 5.00E−04 | 21.0 | 13 | 13 | 100.0 | 1.000 |
| F | 5.00E−05 | 2.1 | 13 | 13 | 100.0 | 0.848 |
| G | 5.00E−06 | 0.21 | 13 | 8 | 61 5 | 0.216 |
| H | 5.00E−07 | 0.021 | 13 | 0 | 0.0 | 0.166 |
| I | 5.00E−08 | 0.0021 | 13 | 0 | 0.0 | 0.162 |
| J | 5.00E−09 | 0.00021 | 13 | 0 | 0.0 | 0.162 |

[a]Estimation based on the total RBC count of patient blood used for spiking (4.14 × 10$^6$ RBC/µl).
[b]Probit 95% hit rate: 6.50E−5 (%) parasitemia, or 2.7 parasites/µl of blood sample.

TABLE 2

*B. microti DNA PCR: Intra-assay and inter-assay reproducibility.*

| Parasitemia (%) Level | Intra-assay (Ct) | | | Inter-assay (Ct) | | |
|---|---|---|---|---|---|---|
| | Ave | StdDev | CV | Ave | StdDev | CV |
| 5.0 × E−3 | 28.2 | 0.12 | 0.4% | n/a | n/a | n/a |
| 5.0 × E−4 | 31.5 | 0.21 | 0.7% | 31.6 | 0.35 | 1.1% |
| 5.0 × E−5 | 35.2 | 0.56 | 1.6% | 35.4 | 0.82 | 2.3% |
| BABLP (low positive control) | n/a | n/a | n/a | 32.1 | 1.3 | 3.9% |

TABLE 3

Accuracy of the *B. microti* DNA real-time PCR for patient specimens compared to results of microscopic examination of Giemsa-stained blood fdms (n = 145).

| | | Giemsa Smear | | |
|---|---|---|---|---|
| | | Positive | Negative | Total |
| *B. microti* DNA PCR | Positive | 15 | 3* | 18 |
| | Negative | 0 | 127 | 127 |
| | Total | 15 | 130 | 145 |

Diagnostic sensitivity 100.0%
Diagnostic specificity: 97.7%*
Diagnostic accuracy: 97.9%*
*Two specimens were positive by PCR at another reference laboratory. The adjusted accuracy of the *B. microti* DNA PCR described in this application was 99.3% (144/145).

TABLE 4

Accuracy of the WMC *B. microti* DNA real-time PCR as compared to the PCR results from a reference laboratory (n = 58)

| | | Wadsworth *B. microti* PCR | | |
|---|---|---|---|---|
| | | Positive | Negative | Total |
| WMC *B. microti* DNA PCR | Positive | 16 | 1* | 17 |
| | Negative | 0 | 41 | 41 |
| | Total | 16 | 42 | 58 |

Diagnostic sensitivity 100.0%
Diagnostic specificity: 97.6%*
Diagnostic accuracy: 98.3%*
*Patient specimen was from a patient recently diagnosed as babesiosis.

TABLE 5

Summary of the performance of *B. microti* DNA PCR in comparison with microscopy for 185 blood samples from 152 patients as routine testing in a prospective study.

| Smear/PCR result | No. of samples | No. of patients |
|---|---|---|
| Smear positive | | |
| Smear positive/PCR positive | 21[a] | 16 |
| Smear positive/PCR negative | 0 | 0 |
| Smear negative | | |
| Smear negative/PCR positive | 21[b] | 3[c] |
| Smear negative/PCR negative | 143 | 133 |
| Total | 185 | 152 |

[a]Included 5 follow-up blood samples from smear-positive patients.
[b]Included 17 follow-up blood samples from 8 previously smear-positive patients and 4 blood samples from 3 smear-negative patients.
[c]Clinical diagnosis of babesiosis was confirmed for all three smear-negative patients based on previous positive-smear (n = 2) or detection of *B. microti*-specific-IgG and IgM antibodies (n = 1).

REFERENCES

1. Homer, M. J., I. Aguilar-Delfin, S. R. Telford, 3rd, P. J. Krause, and D. H. Persing. 2000. Babesiosis. Clin Microbiol Rev 13:451-469.
2. Vannier, E., and P. J. Krause. 2012. Human babesiosis. N Engl J Med 366:2397-2407.
3. Krause, P. J., A. Spielman, S. R. Telford, 3rd, V. K. Sikand, K. McKay, D. Christianson, R. J. Pollack, P. Brassard, J. Magera, R. Ryan, and D. H. Persing. 1998. Persistent parasitemia after acute babesiosis. N Engl J Med 339:160-165.
4. Feder, H. M., Jr., M. Lawlor, and P. J. Krause. 2003. Babesiosis in pregnancy. N Engl J Med 349:195-196.
5. Joseph, J. T., K. Purtill, S. J. Wong, J. Munoz, A. Teal, S. Madison-Antenucci, H. W. Horowitz, M. E. Aguero-Rosenfeld, J. M. Moore, C. Abramowsky, and G. P. Wormser. 2012. Vertical transmission of *Babesia microti*, United States. Emerg Infect Dis 18:1318-1321.
6. Leiby, D. A. 2011. Transfusion-transmitted *Babesia* spp.: bull's-eye on *Babesia microti*. Clin Microbiol Rev 24:14-28.
7. Gubernot, D. M., H. L. Nakhasi, P. A. Mied, D. M. Asher, J. S. Epstein, and S. Kumar. 2009. Transfusion-transmitted babesiosis in the United States: summary of a workshop. Transfusion 49:2759-2771.
8. Herwaldt, B. L., J. V. Linden, E. Bosserman, C. Young, D. Olkowska, and M. Wilson. 2011. Transfusion-associated babesiosis in the United States: a description of cases. Ann Intern Med 155:509-519.
9. Bogoch, I I, B. T. Davis, and D. C. Hooper. 2012. Severe babesiosis in a patient treated with a tumor necrosis factor alpha antagonist. Clin Infect Dis 54:1215-1216.
10. Joseph, J. T., S. S. Roy, N. Shams, P. Visintainer, R. B. Nadelman, S. Hosur, J. Nelson, and G. P. Wormser. 2011. Babesiosis in Lower Hudson Valley, N.Y., USA. Emerg Infect Dis 17:843-847.
11. Kogut, S. J., C. D. Thill, M. A. Prusinski, J. H. Lee, P. B. Backerson, J. L. Coleman, M. Anand, and D. J. White. 2005. *Babesia microti*, upstate New York. Emerg Infect Dis 11:476-478.
12. Zintl, A., G. Mulcahy, H. E. Skerrett, S. M. Taylor, and J. S. Gray. 2003. *Babesia divergens*, a bovine blood parasite of veterinary and zoonotic importance. Clin Microbiol Rev 16:622-636.
13. Kamau, E., L. S. Tolbert, L. Kortepeter, M. Pratt, N. Nyakoe, L. Muringo, B. Ogutu, J. N. Waitumbi, and C. F. Ockenhouse. 2011. Development of a highly sensitive genus-specific quantitative reverse transcriptase real-time PCR assay for detection and quantitation of *plasmodium* by amplifying RNA and DNA of the 18S rRNA genes. J Clin Microbiol 49:2946-2953.
14. Persing, D. H., D. Mathiesen, W. F. Marshall, S. R. Telford, A. Spielman, J. W. Thomford, and P. A. Conrad. 1992. Detection of *Babesia microti* by polymerase chain reaction. J Clin Microbiol 30:2097-2103.
15. Krause, P. J., S. Telford, 3rd, A. Spielman, R. Ryan, J. Magera, T. V. Rajan, D. Christianson, T. V. Alberghini, L. Bow, and D. Persing. 1996. Comparison of PCR with blood smear and inoculation of small animals for diagnosis of *Babesia microti* parasitemia. J Clin Microbiol 34:2791-2794.
16. Johnson, S. T., R. G. Cable, and D. A. Leiby. 2012. Lookback investigations of *Babesia microti*-seropositive blood donors: seven-year experience in a *Babesia*-endemic area. Transfusion 52:1509-1516.

17. Teal, A. E., A. Habura, J. Ennis, J. S. Keithly, and S. Madison-Antenucci. 2012. A new real-time PCR assay for improved detection of the parasite *Babesia microti*. J Clin Microbiol 50:903-908.
18. Rollend, L., S. J. Bent, P. J. Krause, S. Usmani-Brown, T. K. Steeves, S. L. States, T. Lepore, R. Ryan, F. Dias, C. Ben Mamoun, D. Fish, and M. A. Diuk-Wasser. 2013. Quantitative PCR for Detection of *Babesia microti* in *Ixodes scapularis* Ticks and in Human Blood. Vector Borne Zoonotic Dis. 13, 2097-103.
19. Bloch, E. M., T. H. Lee, P. J. Krause, S. R. Telford, 3rd, L. Montalvo, D. Chafets, S. Usmani-Brown, T. J. Lepore, and M. P. Busch. 2013. Development of a real-time polymerase chain reaction assay for sensitive detection and quantitation of *Babesia microti* infection. Transfusion 53:2299-2306.
20. Chan K., Marras S. A., Parveen N., 2013. Sensitive multiplex PCR assay to differentiate Lyme spirochetes and emerging pathogens *Anaplasma phagocytophilum* and *Babesia microti*. BMC Microbiol. 13, 295.
21. Hojgaard A., Lukacik G., Piesman J., 2014. Detection of *Borrelia burgdorferi, Anaplasma phagocytophilum* and *Babesia microti*, with two different multiplex PCR assays. Ticks Tick Borne Dis. 5, 349-51.
22. Lin C. H., Chen Y. C., Pan T. M., 2011. Quantification bias caused by plasmid DNA conformation in quantitative real-time PCR assay. PLoS One. 6, e29101.
23. Yun J. J., Heisler L. E., Hwang, I I, Wilkins O., Lau S. K., Hyrcza M., Jayabalasingham B., Jin J., McLaurin J., Tsao M. S., Der S. D., 2006. Genomic DNA functions as a universal external standard in quantitative real-time PCR. Nucleic Acids Res. 34, e85.
24. Cornillot, E., K. Hadj-Kaddour, A. Dassouli, B. Noel, V. Ranwez, B. Vacherie, Y. Augagneur, V. Bres, A. Duclos, S. Randazzo, B. Carcy, F. Debierre-Grockiego, S. Delbecq, K. Moubri-Menage, H. Shams-Eldin, S. Usmani-Brown, F. Bringaud, P. Wincker, C. P. Vivares, R. T. Schwarz, T. P. Schetters, P. J. Krause, A. Gorenflot, V. Berry, V. Barbe, and C. Ben Mamoun. 2012. Sequencing of the smallest Apicomplexan genome from the human pathogen *Babesia microti*. Nucleic Acids Res 40:9102-9114.

What is claimed is:

1. A method of detecting *Babesia microti* (*B. microti*) using real-time polymerase chain reaction comprising amplifying nucleic acid from *B. microti* using forward primer CGCGTGGCGTTTTATTAGACTT (SEQ ID NO:1), reverse primer CAAAGCCATGCGATTCGC (SEQ ID NO:2), and probe CCAACCCTTCGGGTAATCGGT-GATTC (SEQ ID NO:3) to thereby detect *B. microti*.

2. The method of claim 1, wherein *B. microti* is detected in a sample from blood.

3. The method of claim 1, wherein the method is performed on a blood sample from a human patient or from a blood bank.

4. The method of claim 1, wherein the probe is labelled with a fluorescent reporter that permits detection only after hybridization of the probe with its complementary sequence.

5. The method of claim 1, wherein the probe is labelled at the 3' terminal with tetramethylrhodamine and at the 5' terminal with 6-carboxyfluorescein.

* * * * *

SEQUENCE LISTING

<160> NUMBER OF SEQ ID NOS: 22

<210> SEQ ID NO 1
<211> LENGTH: 21
<212> TYPE: DNA
<213> ORGANISM: Babesia microti

<400> SEQUENCE: 1
cgcgtggcgt ttattagact t                                       21

<210> SEQ ID NO 2
<211> LENGTH: 18
<212> TYPE: DNA
<213> ORGANISM: Babesia microti

<400> SEQUENCE: 2
caaagccatg cgattcgc                                           18

<210> SEQ ID NO 3
<211> LENGTH: 26
<212> TYPE: DNA
<213> ORGANISM: Babesia microti

<400> SEQUENCE: 3
ccaacccttc gggtaatcgg tgattc                                  26

<210> SEQ ID NO 4
<211> LENGTH: 92
<212> TYPE: DNA
<213> ORGANISM: Babesia species, isolate MO1

<400> SEQUENCE: 4
ggccttttgg cggcgtttat tagttctaaa accatccctt tggtttttcg gtgattcata    60
ataaacttgc gaatcgcaat tttttgcgat gg                                  92

<210> SEQ ID NO 5
<211> LENGTH: 92
<212> TYPE: DNA
<213> ORGANISM: Babesia divergens

<400> SEQUENCE: 5

```
ggccttttgg cggcgtttat tagttctaaa accatccctt ttggttttcg gtgattcata      60
ataaacttgc gaatcgcaat tttttgcgat gg                                    92

<210> SEQ ID NO 6
<211> LENGTH: 91
<212> TYPE: DNA
<213> ORGANISM: Babesia species, isolate EU1

<400> SEQUENCE: 6
ggccttttgg cggcgtttat tagttctata accacccttt tggttttcgg tgattcataa      60
taaactcgcg aatcgcaatt tattgcgatg g                                     91

<210> SEQ ID NO 7
<211> LENGTH: 92
<212> TYPE: DNA
<213> ORGANISM: Babesia odocoilei

<400> SEQUENCE: 7
ggcctttttg gcggcgttta ttagttctaa accatccgtt ttggttttcg gtgattcata      60
ataaactcgc gaatcgcaat ttattgcgat gg                                    92

<210> SEQ ID NO 8
<211> LENGTH: 86
<212> TYPE: DNA
<213> ORGANISM: Babesia gibsoni

<400> SEQUENCE: 8
ggcctttttg gcggcgttta ttagttctaa acctcccttg ttttcggtg attcataata       60 aactcgcgaa tcgcttttag cgatgg                                           86

<210> SEQ ID NO 9
<211> LENGTH: 86
<212> TYPE: DNA
<213> ORGANISM: Babesia canis

<400> SEQUENCE: 9
ggccttttgg ccgcgtttat tagttgtaaa cctccgcttg ttttcggtg attcataata       60 aacttgcgaa tcgcttttag cgatgg                                           86

<210> SEQ ID NO 10
<211> LENGTH: 82
<212> TYPE: DNA
<213> ORGANISM: Babesia caballi

<400> SEQUENCE: 10
tgccttttgg cggcgtttat tagttttaa cccttatttt cggtgattca taataaactt       60
gcgaatcgct tttgagcgat gg                                               82

<210> SEQ ID NO 11
<211> LENGTH: 81
<212> TYPE: DNA
<213> ORGANISM: Babesia bigemina

<400> SEQUENCE: 11
ggccttttgg cggcgtttat tagttcgtta accacttttt ctggtgattc ataataaact      60
tgcgaatcgc ttttgcgatg t                                                81

<210> SEQ ID NO 12
<211> LENGTH: 63
```

```
<212> TYPE: DNA
<213> ORGANISM: Babesia bovis

<400> SEQUENCE: 12
gggttttccc gcgtttactg gtcttgtgat ttacagtaac ctgcgactcg cttttttgcga    60 tat                                                                  63

<210> SEQ ID NO 13
<211> LENGTH: 102
<212> TYPE: DNA
<213> ORGANISM: Babesia equi

<400> SEQUENCE: 13
gctgtttaca gttgcgttta ttagacctaa aacctccccg cttctgcggt gtttcggtga    60
ttcataataa attagcgaat cgcatggctt tgccggcgat gt                      102

<210> SEQ ID NO 14
<211> LENGTH: 99
<212> TYPE: DNA
<213> ORGANISM: Babesia microti

<400> SEQUENCE: 14
ggcgcgtttt cgcgtggcgt ttattagact ttaaccaacc cttcgggtaa tcggtgattc    60
ataataaatt agcgaatcgc atggctttgc cggcgatgt                           99

<210> SEQ ID NO 15
<211> LENGTH: 99
<212> TYPE: DNA
<213> ORGANISM: Babesia microti, isolate ATCC 30222

<400> SEQUENCE: 15
ggcgcgtttt cgcgtggcgt ttattagact ttaaccaacc cttcgggtaa tcggtgattc    60
ataataaatt agcgaatcgc atggctttgc cggcgatgt                           99

<210> SEQ ID NO 16
<211> LENGTH: 99
<212> TYPE: DNA
<213> ORGANISM: Babesia microti, isolate Gray

<400> SEQUENCE: 16
ggcgcgtttt cgcgtggcgt ttattagact ttaaccaacc cttcgggtaa tcggtgattc    60
ataataaatt agcgaatcgc atggctttgc cggcgatgt                           99

<210> SEQ ID NO 17
<211> LENGTH: 99
<212> TYPE: DNA
<213> ORGANISM: Babesia microti, isolate Jena

<400> SEQUENCE: 17
ggcgcgtttt cgcgtggcgt ttattagact ttaaccaacc cttcgggtaa tcggtgattc    60
ataataaatt agcgaatcgc atggctttgc cggcgatgt                           99

<210> SEQ ID NO 18
<211> LENGTH: 111
<212> TYPE: DNA
<213> ORGANISM: Babesia microti

<400> SEQUENCE: 18
ggcatatact tctgtatatg tggcgtttat tagacttctt aaccaacccc ttttgggttt    60
```

```
actcggtgat tcataataaa ttagcgaatc gcatggtyct accggcgata t        111

<210> SEQ ID NO 19
<211> LENGTH: 109
<212> TYPE: DNA
<213> ORGANISM: Babesia species, isolate WA1

<400> SEQUENCE: 19
ggccttggct tctgtcttgg ctgcgtttat tagactcgaa accttcccgc ttgcggtact    60
cggtgattca taataaattt gcgaatcgca tggctttttgc cggcgatgg              109

<210> SEQ ID NO 20
<211> LENGTH: 24
<212> TYPE: DNA
<213> ORGANISM: Homo sapiens

<400> SEQUENCE: 20
cctgccaaat atgatgacat caag                                          24

<210> SEQ ID NO 21
<211> LENGTH: 19
<212> TYPE: DNA
<213> ORGANISM: Homo sapiens

<400> SEQUENCE: 21
gtggtcgttg agggcaatg                                                19

<210> SEQ ID NO 22
<211> LENGTH: 27
<212> TYPE: DNA
<213> ORGANISM: Homo sapiens

<400> SEQUENCE: 22
ctcctctgac ttcaacagcg acaccca                                       27
```